US010562840B2

(12) United States Patent
Cermak et al.

(10) Patent No.: US 10,562,840 B2
(45) Date of Patent: Feb. 18, 2020

(54) BIO-BASED ESTOLIDE COMPOSITIONS

(71) Applicant: The United States of America, as represented by the Secretary of Agriculture, Washington, DC (US)

(72) Inventors: Steven C. Cermak, Galesburg, IL (US); Terry Isbell, Elmwood, IL (US); Amber L. Durham, Washington, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 16/139,723

(22) Filed: Sep. 24, 2018

(65) Prior Publication Data

US 2019/0092715 A1 Mar. 28, 2019

Related U.S. Application Data

(60) Provisional application No. 62/564,627, filed on Sep. 28, 2017.

(51) Int. Cl.
| | |
|---|---|
| *C07C 69/675* | (2006.01) |
| *C07C 69/732* | (2006.01) |
| *C10M 129/78* | (2006.01) |
| *C10M 101/04* | (2006.01) |
| *C10M 105/42* | (2006.01) |
| *C07C 69/716* | (2006.01) |
| *C07C 69/73* | (2006.01) |

(52) U.S. Cl.
CPC .......... *C07C 69/675* (2013.01); *C07C 69/716* (2013.01); *C07C 69/73* (2013.01); *C07C 69/732* (2013.01); *C10M 101/04* (2013.01); *C10M 105/42* (2013.01); *C10M 129/78* (2013.01); *C10M 2203/1025* (2013.01); *C10M 2207/30* (2013.01); *C10M 2207/301* (2013.01); *C10M 2207/402* (2013.01); *C10M 2209/1026* (2013.01); *C10N 2220/022* (2013.01); *C10N 2220/023* (2013.01); *C10N 2220/10* (2013.01); *C10N 2230/02* (2013.01); *C10N 2230/10* (2013.01); *C10N 2230/20* (2013.01); *C10N 2230/64* (2013.01); *C10N 2240/04* (2013.01); *C10N 2240/08* (2013.01); *C10N 2240/30* (2013.01)

(58) Field of Classification Search
CPC ..... C07C 69/675; C07C 69/73; C07C 69/716; C07C 69/732; C10M 105/42; C10M 101/04; C10M 129/78; C10M 2209/1026; C10M 2207/301; C10M 2203/1025; C10M 2207/402; C10M 2207/30; C10N 2230/10; C10N 2240/08; C10N 2240/30; C10N 2230/20; C10N 2240/04; C10N 2230/64; C10N 2220/022; C10N 2230/02; C10N 2220/023; C10N 2220/10
See application file for complete search history.

(56) References Cited

U.S. PATENT DOCUMENTS

| | | | |
|---|---|---|---|
| 6,316,649 B1 * | 11/2001 | Cermak | ............... C10M 101/04 508/485 |
| 8,173,825 B2 | 5/2012 | Erhan et al. | |
| 2011/0282084 A1 | 11/2011 | Potula et al. | |
| 2016/0264902 A1 | 9/2016 | Bredsguard et al. | |

FOREIGN PATENT DOCUMENTS

WO      2012173665 A1     12/2012

OTHER PUBLICATIONS

International Searching Authority, PCT/US2018/052783 for the United States of America, as represented by the Secretary of Agriculture, International Filing Date Sep. 26, 2018.
Cermak, S.C. et al., "Physical Properties of Saturated Estolides and their 2-ethylhexyl Esters", (2002) Industrial Crops and Products 16:119-127.

\* cited by examiner

*Primary Examiner* — Taiwo Oladapo
(74) *Attorney, Agent, or Firm* — John Fado; G. Byron Stover

(57) ABSTRACT

Levulinic-capped estolides having improved physical properties that make them more desirable and suitable as bio-based industrial or commercial products are disclosed. The physical properties of the disclosed estolide compositions have surprisingly low pour points that are substantially lower than previously known estolide compounds and superior to petroleum-based compounds designed for similar applications.

21 Claims, No Drawings

BIO-BASED ESTOLIDE COMPOSITIONS

CROSS REFERENCE TO RELATED APPLICATION

This application claims priority to U.S. Provisional Patent Application Ser. No. 62/564,627, filed Sep. 28, 2017, the content of which is incorporated herein by reference in its entirety.

FIELD OF THE INVENTION

The disclosed invention relates generally to novel bio-based estolide compositions having improved physical properties and methods of making such compositions. More specifically, the invention relates to bio-based levulinic-capped estolide compositions for use as biodegradable base stocks and lubricants among other applications.

BACKGROUND OF THE INVENTION

Bio-based products must have comparable or superior characteristics as compared to conventional products to be competitive and accepted in the marketplace. Bio-based lubricants, in particular, must have low pour point temperatures, desirable viscosity, and thermal stability, for example, to be viable alternatives to petroleum-based products. Vegetable oils alone are a functional lubricant; however, they typically have low resistance to thermal oxidative stability (see e.g., Becker, R. & Knorr, A., 1996. An evaluation of antioxidants for vegetable oils at elevated temperatures. Lubr. Sci. 8, 95-117) and poor low temperature performance (see e.g., Asadauskas, S. & Erhan, S. Z., 1999. Depression of pour points of vegetable oils by blending with diluents used for biodegradable lubricants. J. Am. Oil Chem. Soc. 76, 313-316; Zehler, G. R., 2001. Performance tiering of biodegradable hydraulic fluids. Lubricants World September, 22-26). These desired properties sometimes can be improved with additives, but at the expense of biodegradability, toxicity, and price.

With increasing demand for bio-based materials, weaknesses in performance and physical characteristics must be overcome for effective application in industrial and commercial environments. Synthetic esters, such as polyol esters and adipates, low viscosity poly alpha olefins (PAO), such as PAO 2, vegetable oils, especially canola oil, and oleates, for instance, are used industrially as biodegradable basestocks to formulate lubricants. Lubricants usually contain 80-100 wt % basestock and 0-20 wt % additives to tailor viscometric properties, low temperature behavior, oxidative and thermal stability, corrosion protection, demulsibility and water rejection, friction coefficients, lubricities, wear protection, air release, color, and other properties. Biodegradability, however, cannot be improved by using additives.

Estolide compositions have overcome some of these shortcomings without the addition of expensive additives/adjuvants and have shown great promise for use in a wide variety of products with varying physical properties, such as edible applications, cooling fluids, cosmetics, hydraulic fluids, inks, crankcase lubricants, and coatings, among other applications. Nonetheless, there still exists an ongoing need for further improved high-performance bio-based products formulated with renewable agricultural materials (e.g., plant-based oils and animal-based oils) that are economically feasible and sustainable. There is a particular need for such products that exhibit high performance in cold weather applications and thermally harsh conditions.

SUMMARY OF THE INVENTION

To address these challenging issues, the present invention provides levulinic-capped estolides having improved physical properties that make them more desirable and suitable as bio-based industrial or commercial products. The physical properties of the disclosed estolide compositions have surprisingly low pour points that are substantially lower than previously known estolide compounds and are superior to petroleum-based compounds designed for similar applications.

In an aspect, this invention is a composition comprising at least one compound having the formula:

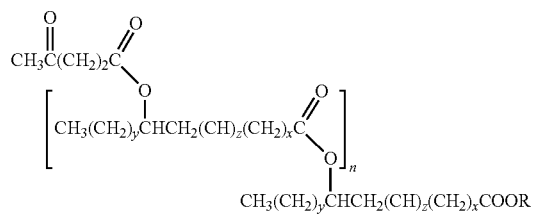

wherein x is an integer from 1 to 11 and y is 14−(x+z) for oleic/castor-based residues, 16−(x+z) for lequerella-based residues, or 18−(x+z) for erucic-based residues; z is 0 or 2, and if z is 2 there is a C=C double bond between the respective carbons; n is 0 or an integer from 1 to about 9; R is selected from the group consisting of: CHR1R2, a residual fragment of lesquerella oil, a residual fragment of castor oil, a residual fragment of erucic oil, or combinations thereof; R1 and R2 are independently selected from hydrogen and a saturated or unsaturated, branched or straight chain, and substituted or unsubstituted hydrocarbon chain of C-1 to C-36; and wherein the predominant species of secondary ester linkage is at the 9 position if z=0, x=6, and y=8; 10 position if z=0, x=7, and y=7; 12 position if z=2, x=7, and y=5 or z=0, x=9, and y=5; 13 position if z=0, x=10, and y=8; and 14 position if z=2, x=9, and y=5 or z=0, x=11, and y=5.

It is an advantage of the invention to provide novel estolides and estolide esters having favorable physical properties as compared to commercially available industrial products such as soy-based fluids and petroleum-based fluids.

It is another advantage of the present invention to provide novel estolides and estolide esters that are cost effective to synthesize and exhibit desirable physical properties, such as pour and cloud points, viscosity, viscosity index, and other low temperature properties.

It is a further advantage of the present invention to provide a novel family of estolide compounds having superior properties for use as lubricant base stocks with reduced or eliminated use of undesirable additives.

An additional advantage of the invention is to provide novel levulinic-capped materials with superior biodegradability and lubricating properties over petroleum-based and other similar commercially available products based on their low temperature properties.

Yet another advantage of the invention is to provide a novel class of levulinic-capped estolide compounds compatible with many other types of fatty acids, hydroxy fatty acids, and/or hydroxy triglyceride materials.

A further advantage of the present invention is to provide novel estolide compounds having a ketone functionality which allows chemical modification and derivative formation to produce more advanced and complex industrial molecules and materials.

This summary is provided to introduce a selection of concepts in a simplified form that are further described below in the detailed description. This summary is not intended to identify all key or essential features of the claimed subject matter, nor is it intended to limit the scope of the claimed subject matter.

DETAILED DESCRIPTION OF THE INVENTION

Unless herein defined otherwise, all technical and scientific terms used herein generally have the same meaning as commonly understood by one of ordinary skill in the art to which this invention belongs. The definitions below may or may not be used in capitalized as well as singular or plural form herein and are intended to be used as a guide for one of ordinary skill in the art to make and use the invention and are not intended to limit the scope of the claimed invention. Mention of trade names or commercial products herein is solely for the purpose of providing specific information or examples and does not imply recommendation or endorsement of such products.

"Estolide" refers to molecules formed when the carboxylic acid functionality of one fatty acid links to the site of unsaturation of another fatty acid to form esters, and a secondary ester linkage is also formed between fatty acid chains. The fatty acid chains are part of an oil in at least one embodiment.

"Estolide Number" or "EN" refers to the extent of oligomerization of estolides. It is one less than the number of fatty acids stacked in the molecule and represents the actual number of estolide linkages in the molecule. For example, EN=1 is an estolide that has one fatty acid capped with only one fatty acid and EN=2 is a fatty acid that is capped with an acyl moiety which is already an estolide with an EN=1.

"Levulinic Acid" or "LA" refers to an organic acid represented by the formula: $CH_3COCH_2CH_2COOH$. It is generally synthesized by heating hexoses or starch in dilute acid (e.g., HCl or $H_2SO_4$) using methods known in the art.

"Residual Fragment" refers to at least one acyl moiety which is typical in compositions of the oil of reference and the acyl moiety could contain estolide(s).

"Secondary Ester Linkage" refers to a fatty acyl molecule attached to the alkyl backbone of another fatty acid fragment attached at a secondary carbon.

"Substituted" refers to molecules which have at least one substituent other than hydrogen on at least one carbon atom within a carbon chain. For example, 2-ethylhexanol ester, neopentanol ester, isobutanol ester, the like and combinations thereof.

"Unsubstituted" refers to molecules which lack at least one substituent.

The disclosed estolide compounds are characterized by surprisingly superior low temperature properties and are intended for use generally in industrial materials, such as lubricant base stocks, hydraulic fluids, gear lubricants, 2-cycle oils, chain lubricants, and track lubricants, without the need for fortifying additives normally required to improve the lubricating properties of conventional base stocks. The disclosed materials may also be used in other applications, including for example, inks, electrical conducting fluids, refrigerant fluids, and other fluid applications. However, it should be appreciated that additives may be beneficial for certain applications according to alternative embodiments as further described herein.

A general reaction scheme for producing the compositions of the invention comprising levulinic-capped estolides includes at least one fatty acid and/or oil as starting material which is reacted with levulinic acid in the presence of a catalyst to form levulinic-capped estolide compositions as described in more detail in the examples below. The catalyst may be left out in some embodiments if higher reaction temperatures and times are used; however, other byproducts might be produced in the absence of catalyst. Specific non-limiting examples of starting materials and their corresponding levulinic-capped products are shown in Table 1. In all cases, the reaction may optionally be doped with additional saturated/unsaturated fatty acids/esters/oils and still obtain the desired levulinic estolides. For example, the oil estolides could be doped with LA and any other fatty acids or oils to get mixed estolides where the oil may contain the LA estolide(s) and estolide(s) from the fatty acids type added. Additionally, one skilled in the art could form a mixture of a host of different hydroxyl esters and acids to get a mixture of different estolides (e.g., lesquerella esters+ saturated castor esters+LA could yield a lesquerella-castor-LA estolide, castor-lesquerella-LA estolide, castor-castor-LA estolide, and/or lesquerella-lesquerella-LA estolide for when EN=2).

TABLE 1

| Starting Materials/Catalyst | Levulinic Estolide Ester Product |
| --- | --- |
| Oleic Acid (FFA) + LA + $HClO_4$ + 2-EH | Levulinic oleic estolide ester |
| Saturated Castor Esters + LA + $Sn(Oct)_2$ | Levulinic 12-hydroxystearic (castor) estolide ester |
| Castor Esters + LA + $Sn(Oct)_2$ | Levulinic 12-hydroxyoleic (castor) estolide ester |
| Erucic Esters + LA + $Sn(Oct)_2$ | Levulinic 13-hydroxybehenic (erucic) estolide ester |
| Saturated *Lesquerella* Esters + LA + $Sn(Oct)_2$ | Levulinic 14-hydroxyarachidic (*lesquerella*) estolide ester |
| *Lesquerella* Esters + LA + $Sn(Oct)_2$ | Levulinic 14-hydroxygondoic (*lesquerella*) estolide ester |
| Saturated *Lesquerella* Oil + LA + $Sn(Oct)_2$ | Levulinic 14-saturated *lesquerella* estolide oil |
| Saturated Castor Oil + LA + $Sn(Oct)_2$ | Levulinic 12-saturated castor estolide oil |
| *Lesquerella* Oil + LA + $Sn(Oct)_2$ | Levulinic 14-*lesquerella* estolide oil |
| Erucic Oil + LA + $Sn(Oct)_2$ | Levulinic 13-erucic estolide oil |
| Castor Oil + LA + $Sn(Oct)_2$ | Levulinic 12-castor estolide oil |

Examples of catalysts which may be used in the synthesis of the disclosed composition include strong mineral acids (e.g., $H_2SO_4$), super acids or Brønsted-Lowry acids (e.g., $HClO_4$), and Lewis acids (e.g., $BF_3$). Polymerization catalyst(s) include, for example, $Sn(Oct)_2$.

The production of estolides by various routes is known in the art (see e.g., JAOCS, Vol. 71, No. 1, pp. 169-174 (February 1994); Erhan et al. JAOCS, Vol. 74, No. 3, pp. 249-254 (1997); Isbell et al. JAOCS, Vol. 74, No. 4, pp.

473-476 (1997); U.S. Pat. Nos. 6,018,063 & 6,316,649). It should be understood that general formula below, are generalizations of the estolide backbone structure of the compounds contemplated herein, and that the formulas are intended to encompass normal distributions of reaction products resulting from the various reaction procedures referenced herein. Not intending to be theory bound, it is believed that the surprisingly superior properties of the subject estolide esters are dictated not so much by positions of the linkage and the site of unsaturation, but more by the combination of the degree of oligomerization, decrease in level of unsaturation, the virtual absence of hydroxyl functionalities on the estolide backbone, the nature of the specific ester moiety, and the levulinic capping moiety. However, the process inherently introduces a distribution of secondary linkage positions in the estolide, which in general, affects low temperature and viscometric behavior very favorably. Minor components other than oleic acid, such as linoleic acid or stearic acid may lead to variations in the basic estolide structure shown in the formulas below.

A particular advantage of the disclosed levulinic-capped estolides is their surprisingly low pour point. Comparable materials exhibit substantially higher pour points than the compounds of the invention. Contemplated within the scope of the invention are those estolide esters which are characterized by the following physical properties: viscosity at 40° C. in a range from about 25 cSt (e.g., 25 cSt) to about 330 cSt (e.g., 330 cSt), a preferred range from about 27 cSt (e.g., 27 cSt) to about 203 cSt (e.g., 203 cSt), and a more preferred range from about 27 cSt (e.g., 27 cSt) to about 200 cSt (e.g., 200 cSt); viscosity at 100° C. in a range from about 4 cSt (e.g., 4 cSt) to about 35 cSt (e.g., 35 cSt), a preferred range from about 5.3 cSt (e.g., 5.3 cST) to about 23 cSt (e.g., 23 cSt), and a more preferred range from about 5.4 cSt (e.g., 5.4 cSt) to about 23 cSt (e.g., 23 cSt); viscosity index in a range from at least about 81 (e.g., 81) to about 178 (e.g., 178), a preferred range from about 121 (e.g., 121) to about 152 (e.g., 152), and a more preferred range from about 129 (e.g., 129) to about 149 (e.g., 149); pour point in a range from about −24° C. (e.g., −24° C.). to about −57° C. (e.g., −57° C.), a preferred range from about −24° C. (e.g., −24° C.) to about −51° C. (e.g., −51° C.), and a more preferred range from about −36° C. (e.g., −36° C.) to about −51° C. (e.g., −51° C.); cloud point in a range from about −3° C. (e.g., −3° C.) to about −57° C. (e.g., −57° C.), a preferred range from about −12° C. (e.g., −12° C.) to about −51° C. (e.g., −51° C.), and a more preferred from about −21° C. (e.g., −21° C.) to about −51° C. (e.g., −51° C.); and a biodegradabilty in the OECD Test greater than 70%. Determination of these properties by conventional test procedures are routine and known in the art. Therefore, identification of estolide esters within the scope of the formulas provided herein would be fully within the skill of the ordinary person in the art.

In embodiments, the composition of the invention includes at least one levulinic-capped estolide having the following general formula to include all types of the disclosed estolides (e.g., free acid estolides, HClO$_4$ estolides, estolide esters, and oil estolides).

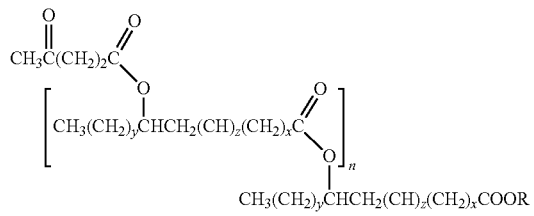

wherein x is an integer from 1 to 11 and y is 14−(x+z) for oleic/castor-based residues, 16−(x+z) for lequerella-based residues, or 18−(x+z) for erucic-based residues; z is 0 or 2, and if z is 2 there is a C═C double bond between the respective carbons; n is 0, 1, or an integer greater than 1 and up to 9 (a preferred range for n is from 0 to 9, a more preferred range is from 0 to about 2 (e.g., 2) 0 to about 3 (e.g., 3), or from 0 to about 5 (e.g., 5)); R is (i) CHR1R2, a residual fragment of lesquerella oil, a residual fragment of castor oil, or combinations thereof, (ii) 2-methylhexyl, (iii) 2-ethylhexyl, or (iv) the backbone of a triglyceride; R1 and R2 are independently selected from hydrogen and a saturated or unsaturated (e.g., the preferred degree of saturation depends on the cost of starting material and the final application, where, for example, for lower pour points some unsaturation is needed but if oxidative stability is a primary concern then lower degrees of unsaturation or no unsaturation is preferred), branched or straight chain (e.g., branching of at least one ester group is preferred for branched embodiments), and substituted or unsubstituted hydrocarbon chain of C-1 to C-36 (e.g., C-6 with branching comprising a 2-ethyl hexyl unit or a triglyceride backbone for estolides from oils). The predominant species of secondary ester linkage is preferably at the 9 or 10 position (e.g., z=0, x=6 or 7, and y=8 or 7, oleic acid-based), or the 12 position (e.g., z=2, x=7, and y=5, castor oil-based; or z=0, x=9, and y=5, saturated castor oil-based), or the 13 position (e.g., z=0, x=10, and y=8, erucic acid-based), or the 14 position (e.g., z=2, x=9, and y=5, lesquerella oil-based; or z=0, x=11, and y=5, saturated lesquerella oil-based). Oleic and castor-based estolides and estolide esters have desirable pour points and are preferred for many applications.

In embodiments, the composition of the invention is a levulinic oleic estolide ester and has the following structure.

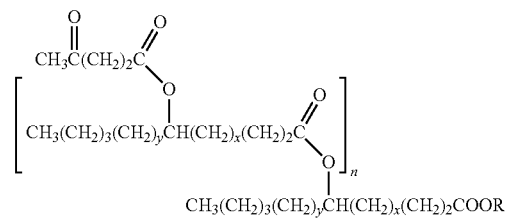

wherein x is an integer from 0 to 10 and y is 10-x, x is preferably 5 or 6 and y is preferably 5 or 4 so the predominant species of secondary ester linkage is in the 9 or 10 position (e.g., if x and y are both 5, the ester linkage is at the 9 position; if x is 6 and y is 4, the ester linkage is at the 10 position); n is 0, 1, or an integer greater than 1 and up to 9 (a preferred range for n is from 0 to 9, a more preferred range is from 0 to about 3 (e.g., 3) or from 0 to about 2 (e.g., 2)); R is CHR1R2; and R1 and R2 are independently selected from hydrogen and a saturated or unsaturated, branched or straight chain (e.g., branching of at least one ester group is preferred for branched embodiments), and substituted or unsubstituted hydrocarbon chain of C-1 to C-36 (e.g., C-6 with branching comprising a 2-ethylhexyl (or 2-methylhexyl) unit or a triglyceride backbone for estolides from oils).

In embodiments, the composition of the invention is a levulinic 12-hydroxystearic (e.g., derived or isolated from castor oil) estolide ester and has the following structure.

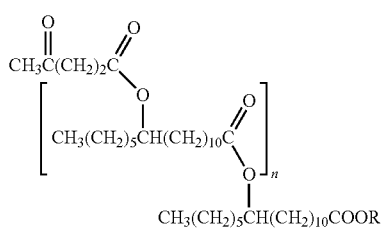

wherein n is 0, 1, or an integer greater than 1 and up to 9 (a preferred range for n is from 0 to 9, a more preferred range is from 0 to about 3 (e.g., 3) or from 0 to about 2 (e.g., 2)); R is CHR1R2; and R1 and R2 are independently selected from hydrogen and a saturated or unsaturated, branched or straight chain (e.g., branching of at least one ester group is preferred for branched embodiments), and substituted or unsubstituted hydrocarbon chain of C-1 to C-36 (e.g., C-6 with branching comprising a 2-ethylhexyl (or 2-methylhexyl) unit or a triglyceride backbone for estolides from oils). The predominant species of secondary ester linkage is preferably at the 12 position.

In embodiments, the composition of the invention is levulinic 12-hydroxyoleic (e.g., derived or isolated from castor oil) estolide ester and has the following structure.

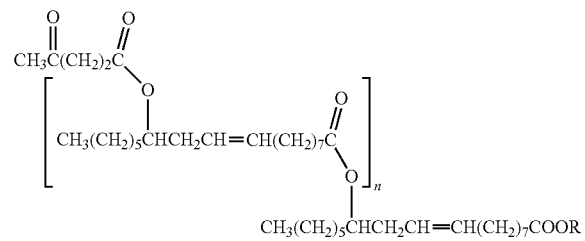

wherein n is 0, 1, or an integer greater than 1 and up to 9 (a preferred range for n is from 0 to 9, a more preferred range is from 0 to about 3 (e.g., 3) or from 0 to about 2 (e.g., 2)); R is CHR1R2; and R1 and R2 are independently selected from hydrogen and a saturated or unsaturated, branched or straight chain (e.g., branching of at least one ester group is preferred for branched embodiments), and substituted or unsubstituted hydrocarbon chain of C-1 to C-36 (e.g., C-6 with branching comprising a 2-ethylhexyl (or 2-methylhexyl) unit or a triglyceride backbone for estolides from oils). The predominant species of secondary ester linkage is preferably at the 12 position and a C=C double bond at the 9 and 10 positions.

In embodiments, the composition of the invention is levulinic 14-hydroxyarachidic (e.g., derived or isolated from lesquerella oil) estolide ester and has the following structure.

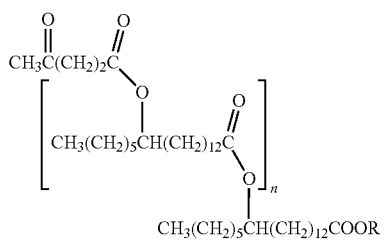

wherein n is 0, 1, or an integer greater than 1 and up to 9 (a preferred range for n is from 0 to 9, a more preferred range is from 0 to about 3 (e.g., 3) or from 0 to about 2 (e.g., 2)); R is CHR1R2; and R1 and R2 are independently selected from hydrogen and a saturated or unsaturated, branched or straight chain (e.g., branching of at least one ester group is preferred for branched embodiments), and substituted or unsubstituted hydrocarbon chain of C-1 to C-36 (e.g., C-6 with branching comprising a 2-ethylhexyl (or 2-methylhexyl) unit or a triglyceride backbone for estolides from oils). The predominant species of secondary ester linkage is preferably at the 14 position.

In embodiments, the composition of the invention is levulinic 13-hydroxybehenic (e.g., derived or isolated from erucic oil) estolide ester and has the following structure.

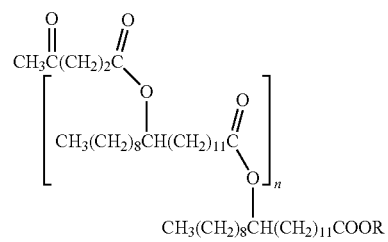

wherein n is 0, 1, or an integer greater than 1 and up to 9 (a preferred range for n is from 0 to 9, a more preferred range is from 0 to about 3 (e.g., 3) or from 0 to about 2 (e.g., 2)); R is CHR1R2; and R1 and R2 are independently selected from hydrogen and a saturated or unsaturated, branched or straight chain (e.g., branching of at least one ester group is preferred for branched embodiments), and substituted or unsubstituted hydrocarbon chain of C-1 to C-36 (e.g., C-6 with branching comprising a 2-ethylhexyl (or 2-methylhexyl) unit or a triglyceride backbone for estolides from oils). The predominant species of secondary ester linkage is preferably at the 13 position.

In embodiments, the composition of the invention is levulinic 14-hydroxygondoic (e.g., derived or isolated from lesquerella oil) estolide ester and has the following structure.

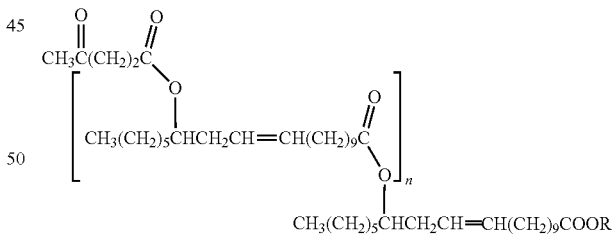

wherein n is 0, 1, or an integer greater than 1 and up to 9 (a preferred range for n is from 0 to 9, a more preferred range is from 0 to about 3 (e.g., 3) or from 0 to about 2 (e.g., 2)); R is CHR1R2; and R1 and R2 are independently selected from hydrogen and a saturated or unsaturated, branched or straight chain (e.g., branching of at least one ester group is preferred for branched embodiments), and substituted or unsubstituted hydrocarbon chain of C-1 to C-36 (e.g., C-6 with branching comprising a 2-ethylhexyl (or 2-methylhexyl) unit or a triglyceride backbone for estolides from oils). The predominant species of secondary ester linkage is preferably at the 14 position and a C=C double bond at the 11 and 12 positions.

In embodiments, the composition of the invention is levulinic 14/13/12-(saturated lesquerella/erucic/saturated castor) estolide oil and has the following structure.

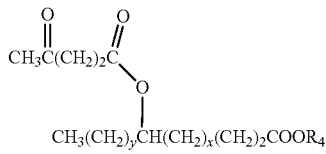

wherein R4 is the residual fragment of saturated lesquerella (x=10 and y=5) oil, erucic (x=9 and y=8 or x=10 and y=7) oil, or saturated castor (x=8 and y=5) oil. The predominant species of secondary ester linkage is at the 14 position (for lesquerella oil), or at the 13/14 position (for erucic oil), or at the 12 position (for saturated castor oil).

In embodiments, the composition of the invention is levulinic 14/12-(lesquerella/castor) estolide oil and has the following structure.

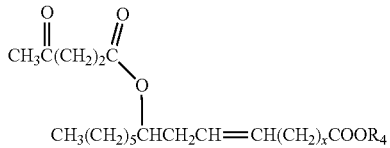

wherein R4 is the residual fragment of lesquerella (x=9) oil or of castor (x=7) oil. The predominant species of secondary ester linkage is preferably at the 14 position (for lesquerella oil) or at the 12 position (for castor oil) and a C=C double bond at the 11 and 12 positions (for lesquerella oil) or at the 9 and 10 positions (for castor oil).

In embodiments, when used as a base stock, the subject estolides of the invention can be admixed with an effective amount of other lubricating agents such as mineral or vegetable oils, other estolides, poly alpha olefins, polyol esters, oleates, diesters, conventional additive packages, bio-based additive packages, other natural or synthetic fluids, the like, and combinations thereof.

According to alternative embodiments, various additives are used in combination with the disclosed levulinic-capped estolide compositions of the invention. In certain cases as determined by a skilled artisan additives, though not preferred, may aid, for example, in addressing contamination, preventing premature breakdown, or increasing protective properties. In most cases where additives are desired, the compositions of the invention generally require small amounts of additives as compared to conventional fluids.

Examples of such additives include detergents, corrosion inhibitors, antioxidants, viscosity modifiers, friction modifiers, pour point depressants, dispersants, anti-foam agents, anti-misting agents, wax crystal modifiers/dewaxing aids, colorants, the like, and combinations thereof.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement. The following examples are intended only to further illustrate the invention and are not intended in any way to limit the scope of the invention as defined by the claims.

Materials

The following materials were used for the examples below. Lesquerella oil was obtained by vacuum filtration of crude cold-pressed L. fendleri seed, pressed in USDA laboratories (Peoria, Ill.). Levulinic acid (98%), oleic acid technical grade (90%), tin (II) 2-ethylhexanoate ($Sn(Oct)_2$), boron trifluoride diethyletherate ($BF_3$), palladium on carbon (Pd/C), and 2-ethylhexanol (2-EH) were purchased from Sigma-Aldrich Co. (St. Louis, Mo.). Castor oil, hexanes, hydrochloric acid, sodium sulfate, sodium chloride, sodium phosphate monobasic monohydrate, sulfuric acid, and potassium hydroxide, and Whatman filter paper were purchased from Fisher Scientific Co. (Fairlawn, N.J.). Perchloric acid (70%) was purchased from Alfa Aesar (Ward Hill, Mass.). 12-hydroxy stearic acid was purchased from Alnoroil Co. Inc. (Valley Stream, N.Y.). Ethyl acetate was obtained from EMD Millipore Co. (Billerica, Mass.). Ethanol was purchased from Decon Labs, Inc. (King of Prussia, Pa.). The fatty acid methyl ester (FAME) standard mixtures were obtained from Nu-Check Prep (Elysian, Minn.). Solvents for chromatography and extraction were HPLC grade or an equivalent, and were used without further purification.

Example 1

Levulinic-capped oleic 2-ethylhexyl estolide esters (Scheme 1: a 2-step process is shown, where the first step is estolide formation and the second step is esterification. R can be, for example, 2-ethylhexyl or 2-methylhexyl). Levulinic capped oleic 2-ethylhexyl estolide esters were synthesized via acid-catalyzed condensation reactions without solvent in a 2,000 mL 3-neck round bottom flask that had been pre-treated with an acidic wash. Oleic acid (150.0 g, 531.9 mmol) and capping material, levulinic acid (309.0 g, 2,660 mmol) were combined together, heated to 60° C. under house vacuum (7.5-10.9 kPa), and stirred with a Teflon coated stir bar. After the desired temperature of 60° C.±0.1° C. was reached, perchloric acid (319 mmol, 27.5 mL, 0.1 eq) was added to the mixture, vacuum restored, and stirred. After 24 hrs, 2-ethylhexanol (498.8 g, 3830 mmol, 600 mL) was added to the flask. The vacuum was restored and the mixture was stirred for an additional 4 h at 60° C.±0.1° C. The reaction was allowed to cool to RT and then quenched by the addition of KOH (20.60 g, 367.1 mmol, 1.15 eq based on HC104) in 90% ethanol/water (100 mL) solution and allowed to stir for at least 30 m. The precipitate was allowed to settle before the product was filtered through a Buchner funnel with Whatman #54 filter paper. The solution pH was then adjusted to be in the range of 5.0 to 6.0 using a pH 5 buffer ($NaH_2PO_4$, 519 g in 4 L $H_2O$). The organic layer was washed with concentrated NaCl solution, dried over sodium sulfate, and filtered with Whatman #54 filter paper. All reactions were concentrated in vacuo and then kugelrohr-distilled at a temperature range of 110° C. to 130° C. at 0.013-0.067 kPa for 1 hr to remove any excess ethanol, 2-ethylhexanol, and levulinic acid. The temperature was then increased to 190° C. at 0.013-0.067 kPa for 3 to 4 hrs to remove any unreacted fatty acids and by-products, such as oleic and levulinic 2-ethylhexyl esters. The final product was then filtered with a Whatman #54 filter paper.

(1)

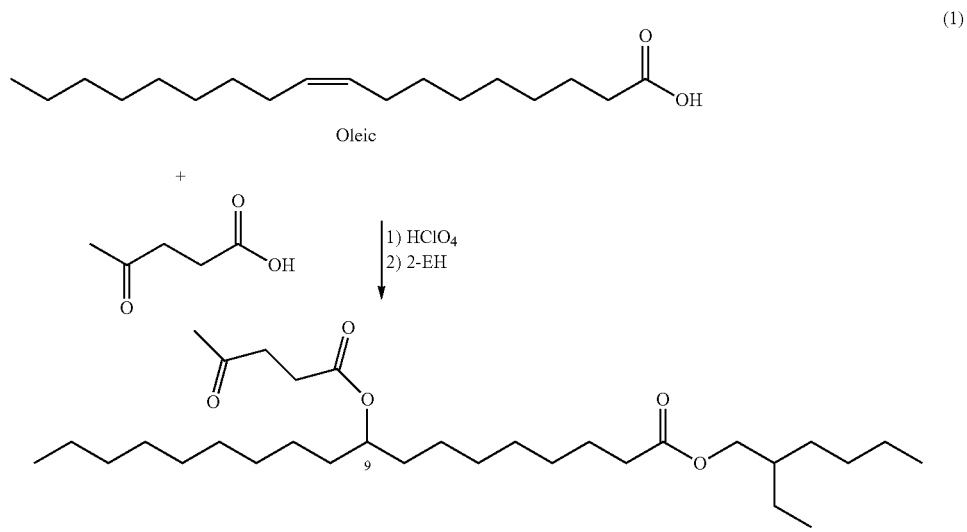

Example 2

12-hydroxystearic (or 14-hydroxyarachidic) 2-ethylhexyl esters and the unsaturated versions from castor and lesquerella sources (Scheme 2: a 2-step process, where the first step is esterification and the second step (shown below) is the estolide formation. R can be, for example, 2-ethylhexyl or 2-methylhexyl). Acid-catalyzed esterification reactions were conducted with solvent, 2-ethylhexanol, in a 5 L three-neck round bottom flask under vacuum. The flask was placed under vacuum (20 Pa) and heated to 80° C. for 8 hrs using a heating mantle controlled by a J-Kem Model Apollo (St. Louis, Mo.) temperature controller utilizing a temperature probe submerged below the liquid level. A solution of boron trifluoride diethyl etherate (0.5 M, 84.0 mL) was added to 12-hydroxystearic acid (868 g, 2.89 mol) and 2-ethylhexanol (1.13 kg, 8.67 mol, 1.35 L). After 8 h, the flask contents were allowed to cool to RT and transferred to a reparatory funnel followed by the addition of 200 mL of a 1:1 ethyl acetate:hexane solution. The pH of the solution was then adjusted to 5.0 to 6.0 using a pH 5 buffer ($NaH_2PO_4$, 519 g in 4 L $H_2O$). The organic layer was then washed with concentrated NaCl solution, dried over sodium sulfate, and filtered with Whatman #54 filter paper. All reactions were concentrated in vacuo and then Kugelrohr-distilled at 90-110° C. at 0.013-0.067 kPa for 2-3 hrs to remove any excess 2-ethylhexanol. The residue then underwent a second Kugelrohr-distillation under vacuum (0.013-0.067 kPa) at 180-200° C. to yield a purified, colorless distillate of 12-hydroxystearic (or 14-hydroxyarachidic) 2-ethylhexyl esters or the unsaturated versions from castor and lesquerella sources.

Levulinic-capped 12-hydroxystearic (or 14-hydroxyarachidic) 2-ethylhexyl estolide esters or the unsaturated versions from castor and lesquerella sources (Scheme 2). The previously synthesized 12-hydroxystearic (or 14-hydroxyarachidic) 2-ethylhexyl esters or the unsaturated versions from castor and lesquerella sources (150.0 g, 364.1 mmol) 1.0 equivalent and the capping material, levulinic acid (211.4 g, 1820 mmol) 5.0 equivalents were combined in a 1 L three-neck round bottom flask. The reaction was catalyzed with 0.48 wt. % tin (II) 2-ethylhexanoate (0.72 g, 1.77 mmol) per gram of ester starting material. The flask was equipped with a magnetic stir bar, temperature probe, and a series of two connected condensers. A circulating bath regulated at 30° C. was connected to the first condenser. The second condenser, cooled with cold tap water, was attached to the first with a 75 degree distilling head. A vacuum distillation adapter and round bottom were fitted on the outlet of the second condenser for collection of water produced from the reaction. The flask was heated to 130° C. under vacuum (20 Pa) with stirring for 24 hrs. The reaction was allowed to cool to RT and was then filtered through Whatman #54 filter paper. The filtered product was placed in a reparatory funnel, after which the unreacted levulinic acid bottom layer was removed. The resulting top layer was Kugelrohr-distilled at 190° C. under vacuum 0.013-0.067 kPa for 2-3 hrs. The residue consisting of levulinic-capped 12-hydroxystearic (or 14-hydroxyarachidic) 2-ethylhexyl estolide esters or the unsaturated versions from castor and lesquerella sources was filtered through Whatman #54 filter paper.

(2)

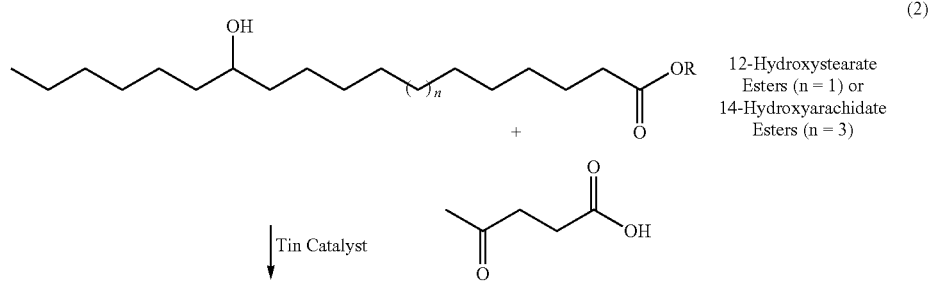

12-Hydroxystearate Esters (n = 1) or
14-Hydroxyarachidate Esters (n = 3)

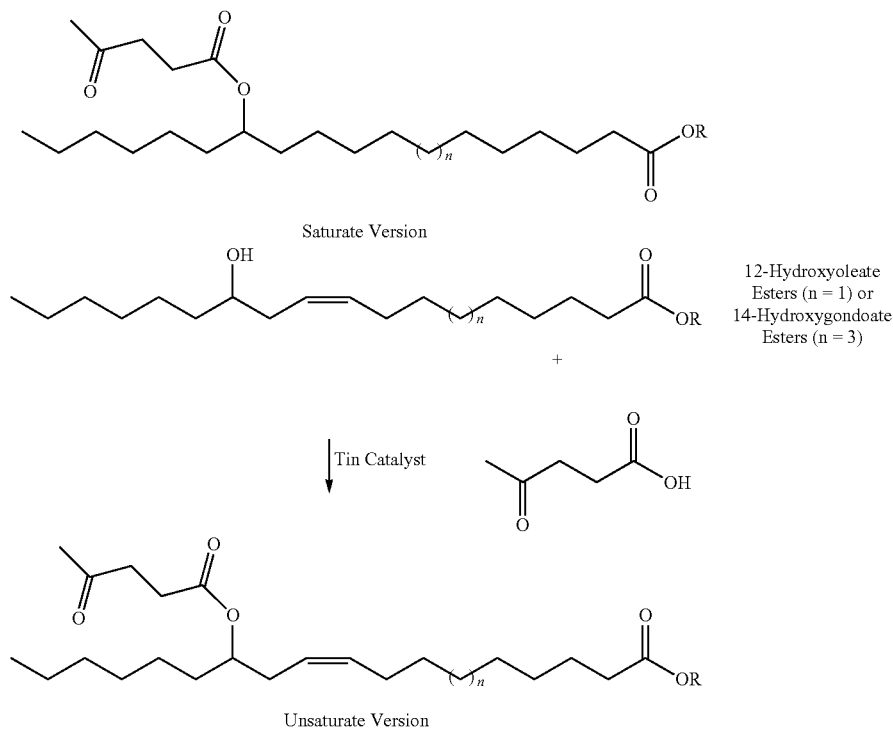

Example 3

Hydrogenation of Lesquerella and Castor Triglycerides (Scheme 3: embodiment with oil shown. R' is residual of original starting triglyceride). Hydrogenation was performed by combining refined, bleached, and deodorized (RBD) lesquerella (or castor) oil (315.0 g, 327.4 mmol), hexane (200 mL), and Pd/C (2.00 g) on activated carbon in a stainless-steel pressure reactor (Pressure Products Industries, Warminster, Pa.). The reactor was charged to 1379 kPa hydrogen after first purging three times with hydrogen. The reactions were heated to 100° C. with stirring for 17-20 hrs.

The product was dissolved in ethyl acetate and separated from the catalyst by vacuum filtration through celite and #50 Whatman filter paper using a double walled Buchner funnel heated with steam. The product was rinsed through the funnel with large amounts of hot ethyl acetate. The resulting product was filtered through #50 Whatman paper using a pressure filter to remove residual amounts of celite and catalyst. All products were concentrated in vacuo and then scraped from sides of round bottom via spatula. The final product was placed under vacuum (6-13 Pa) for 2-3 hrs to remove residual solvent.

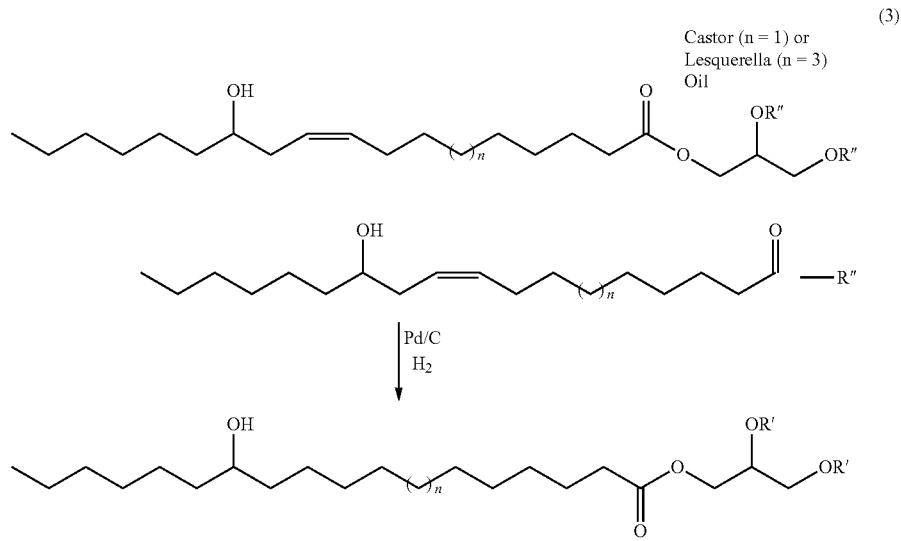

(3)

-continued

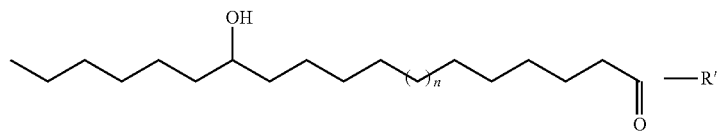

Example 4

Levulinic-capped castor/erucic/lesquerella triglyceride estolide (Scheme 4: embodiment with oil shown. R' is residual of original starting triglyceride). The levulinic-capped castor/erucic/lesquerella triglyceride estolides were synthesized by combining either saturated or unsaturated castor (or lesquerella or erucic) oil (75.0 g, 80.5 mmol) with 10 equivalents of capping material, levulinic acid (93.4 g, 805 mmol) in a 500 mL 3-neck flask. The reaction was catalyzed with 0.48 wt. % tin (II) 2-ethylhexanoate (0.36 g, 0.89 mmol) per gram of castor (or lesquerella or erucic) oil. The flask was equipped with a magnetic stir bar, temperature probe, and a series of two connected condensers. A circulating bath regulated at 60° C. was connected to the first condenser. The second condenser, cooled with cold tap water, was attached to the first with a 75 degree distilling head. A vacuum distillation adapter and round bottom flask were fitted on the outlet of the second condenser for collection of water produced from the reaction. The flask was heated to 150° C. under vacuum (20 Pa) with stirring for 24 hrs. The reaction was allowed to cool to RT and then vacuum filtered through Whatman #54 filter paper. The resulting product was Kugelrohr-distilled at 100° C. under vacuum 0.013-0.067 kPa for 2-3 hrs to remove unreacted levulinic acid. The residue consisting of the levulinic-capped triglyceride estolide was filtered through Whatman #54 filter paper.

(4)

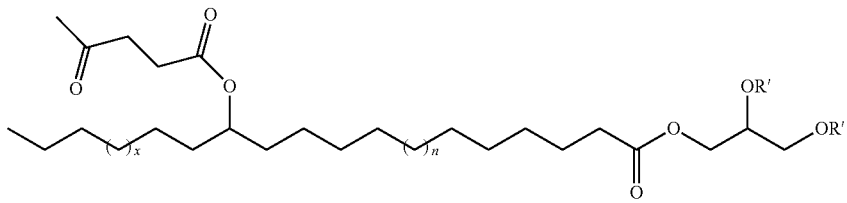

Saturated Castor (n = 1 and x = 1) or
Erucic (n = 2 and x = 4 or n = 3 and x = 3) or
Saturated Lesquerella (n = 3 and x = 1)
Oil Estolides

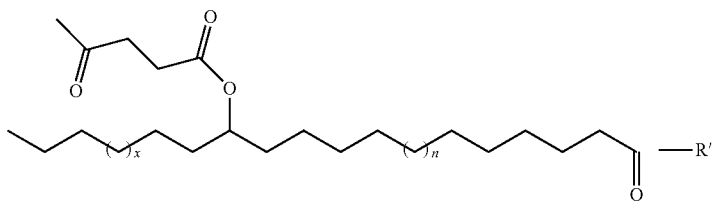

Castor (n = 1) or
Lesquerella (n = 3)
Oil Estolides

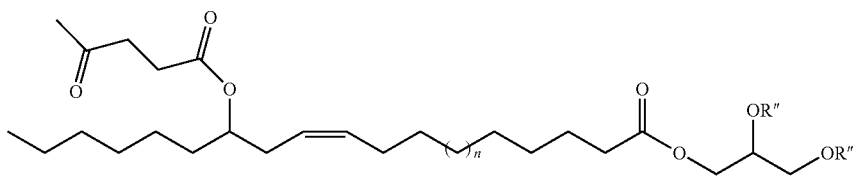

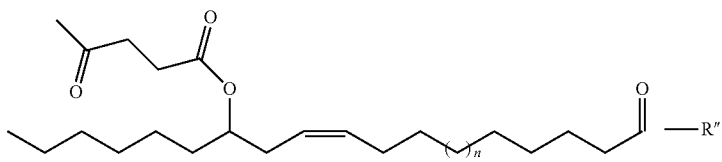

Example 5

This example illustrates various reaction conditions and combinations as illustrated in Table 2. All reactions were allowed to proceed for 24 hrs.

TABLE 2

| SM | SM eq. | Levulinic Acid eq. | Cat. | Cat Wt %. | Cat eq | 2EH eq | Temp ° C. | Rxn, Cond |
|---|---|---|---|---|---|---|---|---|
| Oleic FA | 2 | 1 | $HClO_4$ | — | 0.05 | — | 60 | vac, stir |
| Oleic FA | 2 | 1 | $HClO_4$ | — | 0.05 | 1.2 | 60 | vac, stir |
| 12-OH stearic 2-EH esters | 1 | 1.5 | $Sn(Oct)_2$ | 0.1 | — | — | 130 | vac, stir, 2 conden |
| 12-OH stearic 2-EH esters | 1 | 5 | $Sn(Oct)_2$ | 0.1 | — | — | 130 | vac, stir, 2 conden |
| Oleic FA | 2 | 1 | $HClO_4$ | — | 0.10 | — | 60 | vac, stir |
| Oleic FA | 2 | 1 | $HClO_4$ | — | 0.10 | 1.2 | 60 | vac, stir |
| 12-OH stearic 2-EH esters | 1 | 5 | $Sn(Oct)_2$ | 0.48 | — | — | 150 | vac, stir, 2 conden |
| 12-OH stearic 2-EH esters | 1 | 5 | $Sn(Oct)_2$ | 0.48 | — | — | 130 | vac, stir, 2 conden |
| Oleic FA | 1 | 5 | $HClO_4$ | — | 0.10 | 1.2 | 60 | vac, stir |
| 12-OH stearic 2-EH esters | 1 | 5 | $Sn(Oct)_2$ | 0.48 | — | — | 130 | vac, stir, 2 conden |
| Oleic FA | 1 | 5 | $HClO_4$ | — | 0.10 | 1.2 | 60 | vac, stir |
| 12-OH stearic 2-EH esters | 1 | 5 | $Sn(Oct)_2$ | 0.48 | — | — | 130 | vac, stir, 2 conden |
| 12-OH stearic 2-EH esters | 1 | 5 | $Sn(Oct)_2$ | 0.48 | — | — | 130 | vac, stir, 2 conden |
| Oleic FA | 1 | 5 | $HClO_4$ | — | 0.10 | 1.2 | 60 | vac, stir |
| Oleic FA | 1 | 5 | $HClO_4$ | — | 0.10 | 1.2 | 60 | vac, stir |
| 12-OH stearic 2-EH esters | 1 | 5 | $Sn(Oct)_2$ | 0.48 | — | — | 130 | vac, stir, 2 conden |
| Castor oil | 1 | 5 | $Sn(Oct)_2$ | 0.48 | — | — | 130 | vac, stir, 2 conden |
| Castor oil | 1 | 10 | $Sn(Oct)_2$ | 0.48 | — | — | 140 | vac, stir, 2 conden |
| 12-OH stearic 2-EH esters | 1 | 5 | $Sn(Oct)_2$ | 0.48 | — | — | 130 | vac, stir, 2 conden |
| 12-OH stearic 2-EH esters | 1 | 5 | $Sn(Oct)_2$ | 0.48 | — | — | 130 | vac, stir, 2 conden |
| Oleic FA | 1 | 5 | $HClO_4$ | — | 0.10 | 1.2 | 60 | vac, stir |
| Oleic FA | 1 | 5 | $HClO_4$ | — | 0.10 | 1.2 | 60 | vac, stir |
| Castor oil | 1 | 10 | $Sn(Oct)_2$ | 0.48 | — | — | 150 | vac, stir, 2 conden (both cold) |
| 12-OH stearic 2-EH esters | 1 | 5 | $Sn(Oct)_2$ | 0.48 | — | — | 150 | vac, stir, 2 conden |
| 12-OH stearic 2-EH esters | 1 | 5 | $Sn(Oct)_2$ | 0.48 | — | — | 150 | vac, stir, 2 conden |
| 12-OH stearic 2-EH esters | 1 | 5 | $Sn(Oct)_2$ | 0.48 | — | — | 130 | vac, stir, 2 conden |
| 12-OH stearic 2-EH esters | 1 | 5 | $Sn(Oct)_2$ | 0.48 | — | — | 130 | vac, stir, 2 conden |
| Castor oil | 1 | 10 | $Sn(Oct)_2$ | 0.48 | — | — | 130 | vac, stir, 2 conden |
| Castor oil | 1 | 10 | $Sn(Oct)_2$ | 0.48 | — | — | 130 | vac, stir, 2 conden |
| Castor oil | 1 | 10 | $Sn(Oct)_2$ | 0.48 | — | — | 140 | vac, stir, 2 conden |
| Castor oil | 1 | 10 | $Sn(Oct)_2$ | 0.48 | — | — | 150 | vac, stir, 2 conden |
| Castor oil | 1 | 10 | $Sn(Oct)_2$ | 0.48 | — | — | 150 | vac, stir, 2 con inc to 40° C. |

Example 6

Table 3 in this example illustrates the physical properties of various embodiments of the disclosed composition.

Pour Point. The official ASTM Method D 97-96a was used to measure pour points to an accuracy of ±3° C. The pour points were determined by placing a test jar with 50 mL of the sample into a cylinder submerged in a cooling medium. The sample temperature was measured in 3° C. increments at the top of the sample until the material stopped pouring. This point was determined when the material in the test jar did not flow when held in a horizontal position for 5 s. The pour point was defined as the coldest temperature at which the sample still poured. All pour point measurements were conducted in duplicate and average values reported.

Certain samples exhibited low pour points which were unexpected and surprising. Pour points of biopolymeric lubricants are typically not lower than −23° C. and rarely lower than −36° C. for the most highly branched biopolymers. However, the levulinic-capped materials of the invention exhibited unexpected pour points as low as −57° C. with many derivatives having pour points of less than −50° C. and these samples showed values well below the expected level as illustrated in the presented data.

Cloud Point. The official ASTM Method D 2500-99 was used to measure cloud points to an accuracy of ±1° C. The cloud points were determined by placing a test jar with 50 mL of the sample into a cylinder submerged into a cooling medium. The sample temperature was measured in 1° C. increments at the bottom of the sample until any cloudiness was observed at the bottom of the test jar. The cloud point was defined as the temperature at which a haze or cloud is first observed at the bottom of the test jar. All cloud points were measured in duplicate and average values reported.

Viscosity. Calibrated Cannon-Fenske viscometer tubes obtained from Cannon Instrument Co. (State College, Pa.) were used to measure viscosity. Measurements were run in a Temp-Trol (Precision Scientific, Chicago, Ill.) viscometer bath set at 40 and 100° C. where the bath medium does not vary by more than ±0.02° C. Viscosity and viscosity index were calculated using the official ASTM Methods D 445-97 and ASTM D 2270-93, respectively. Duplicate measurements were made and average values reported.

Acid Values (AV). The 751 GPD Titrino from Metrohm Ltd. (Herisau, Switzerland) was used for measurements. Acid values were determined by the official AOCS Method Te 2a-64 (Firestone, 1994, Official and Tentative Methods of the American Oil Chemists' Society. Fourth ed., AOCS, Champaign, Ill.) with ethanol substituted for methanol to increase the solubility of the estolides during the titration. All acid values were run in duplicate and average values were reported. Free Fatty Acid (FFA) values were calculated from the acid values.

Gardner Color. A Lovibond 3-Field Comparator from Tintometer Ltd. (Salisbury, England) using the official AOCS method Td 1a-64 (Firestone, 1994, Official and Tentative Methods of the American Oil Chemists' Society. Fourth ed., AOCS, Champaign, Ill.) was used for Gardner color measurements. The "+" and "−" notation was employed to designate samples that did not match one particular color.

TABLE 3

| Sample Name | Pour Pt (° C.) | Cloud Pt (° C.) | Viscosity (cSt) 40° C. | Viscosity (cSt) 100° C. | Viscosity Index | AV (mg/g) | FFA (%) | Gardner Color |
|---|---|---|---|---|---|---|---|---|
| Oleic-levulinic 2-EH estolide, 0.05 eq HClO$_4$ | −39 | −27 | 15.4 | 4.0 | 168 | — | — | — |
| 12-OH Stearic 2-EH esters 1 eq, levulinic 1.5 eq (dist 180° C.) | −24 | −22 | 60.6 | 10.8 | 171 | — | — | — |
| 12-OH Stearic 2-EH esters 1 eq, levulinic 5 eq | −12 | 9 | 25.9 | 5.3 | 143 | — | — | — |
| Oleic-levulinic free acid estolide, 0.1 eq HClO$_4$ | −27 | −28 | 264.9 | 27.7 | 138 | — | — | — |
| Oleic-levulinic 2-EH estolide, 0.1 eq HClO$_4$ | −36 | −27 | 39.2 | 7.9 | 178 | — | — | — |
| 12-OH Stearic 2-EH esters 1 eq, levulinic 5 eq, Tin (II) ethylhexanoate 0.48% | −45 | −26 | 35.8 | 6.7 | 146 | 2.59 | 1.30 | 11+ |
| 12-OH Stearic 2-EH esters 1 eq, levulinic 5 eq, Tin (II) ethylhexanoate 0.48% | −15 | 0 | 27.1 | 5.6 | 152 | — | — | — |
| 12-OH Stearic 2-EH esters 1 eq, levulinic 5 eq, Tin (II) ethylhexanoate 0.48% | −45 | −24 | 32.3 | 6.3 | 149 | 0.08 | 0.04 | 2+ |
| Oleic acid 1 eq, levulinic 5 eq, HClO$_4$ 0.1 eq | −51 | −32 | 41.1 | 7.2 | 139 | 2.29 | 1.15 | 13− |
| 12-OH Stearic 2-EH esters 1 eq, levulinic 5 eq, Tin (II) ethylhexanoate 0.48% | −42 | −30 | 27.1 | 5.5 | 145 | 0.95 | 0.48 | 0 |
| Oleic acid 1 eq, levulinic 5 eq, HClO$_4$ 0.1 eq | −57 | −31 | 27.8 | 5.4 | 132 | 2.68 | 1.34 | — |
| 12-OH Stearic 2-EH esters 1 eq, levulinic 5 eq, Tin (II) ethylhexanoate 0.48% | −42 | −11 | 27.4 | 5.6 | 149 | 1.31 | 0.66 | — |
| 12-OH Stearic 2-EH esters 1 eq, levulinic 5 eq, Tin (II) ethylhexanoate 0.48% | −45 | −21 | 29.7 | 5.9 | 148 | 0.81 | 0.41 | 3 |
| Oleic acid 1 eq, levulinic 5 eq, HClO$_4$ 0.1 eq | −48 | −38 | 45.7 | 7.8 | 140 | 3.03 | 1.53 | 17+ |
| 12-OH Stearic 2-EH esters | >20 | >20 | 29.6 | 4.9 | 81 | 0.40 | 0.20 | 0 |
| Oleic acid 1 eq, levulinic 5 eq, HClO$_4$ 0.1 eq | −51 | −27 | 39.3 | 6.9 | 135 | 2.71 | 1.36 | 8 |
| Oleic acid 1 eq, levulinic 5 eq, HClO$_4$ 0.1 eq | −51 | <−53 | 43.1 | 7.4 | 137 | 2.36 | 1.18 | 16− |
| 1:1; 12-OH stearic 2-EH esters:levulinic estolide | 15 | >20 | 27.5 | 5.3 | 128 | 1.08 | 0.54 | — |
| 3:1; 12-OH stearic 2-EH esters:levulinic estolide | 18 | >20 | 27.8 | 5.0 | 105 | 0.70 | 0.35 | — |
| 12-OH Stearic 2-EH esters 1 eq, levulinic 5 eq, Tin (II) ethylhexanoate 0.48% | −45 | −45 | 37.8 | 6.9 | 144 | 1.07 | 0.54 | 9 |
| Castor oil 1 eq, levulinic 5 eq, Tin (II) ethylhexanoate 0.48%, 130° C. | −30 | <−56 | 330.6 | 35.0 | 151 | 1.02 | 0.51 | 11+ |
| Castor oil 1 eq, levulinic 10 eq, Tin (II) ethylhexanoate 0.48%, temp inc to 140° C. | −30 | <−54 | 312.0 | 32.7 | 146 | 2.47 | 1.24 | 13+ |
| 12-OH Stearic 2-EH esters 1 eq, levulinic 5 eq, Tin (II) ethylhexanoate 0.48% | −24 | 0 | 41.4 | 7.4 | 145 | 1.49 | 0.75 | 17 |
| 12-OH Stearic 2-EH esters | >20 | >20 | 30.2 | 5.0 | 85 | 1.46 | 0.73 | 0 |
| 12-OH Stearic 2-EH esters 1 eq, levulinic 5 eq, Tin (II) ethylhexanoate 0.48% | −42 | −19 | 31.3 | 6.0 | 141 | 1.61 | 0.81 | 3 |
| 12-OH Stearic 2-EH esters 1 eq, levulinic 5 eq, Tin (II) ethylhexanoate 0.48% | −42 | −43 | 34.1 | 6.4 | 142 | 1.33 | 0.67 | 6− |
| 12-OH Stearic 2-EH esters 1 eq, levulinic 5 eq, Tin (II) ethylhexanoate 0.48% | −42 | −22 | 48.9 | 6.6 | 81 | 1.64 | 0.82 | 14− |
| 12-OH Stearic 2-EH esters 1 eq, levulinic 5 eq, Tin (II) ethylhexanoate 0.48% | −51 | <−51 | 45.8 | 7.9 | 144 | 1.39 | 0.70 | 12− |
| 12-OH Stearic 2-EH esters 1 eq, levulinic 5 eq, Tin (II) ethylhexanoate 0.48% | −12 | 4 | 25.9 | 5.3 | 143 | 2.15 | 1.08 | 2+ |
| 12-OH Stearic 2-EH esters 1 eq, levulinic 5 eq, Tin (II) ethylhexanoate 0.48% | −27 | −3 | 27.8 | 5.5 | 139 | 1.74 | 0.88 | 4− |
| 12-OH Stearic 2-EH esters 1 eq, levulinic 5 eq, Tin (II) ethylhexanoate 0.48% | −42 | −26 | 30.9 | 6.0 | 144 | 1.57 | 0.79 | 5+ |

TABLE 3-continued

| Sample Name | Pour Pt (° C.) | Cloud Pt (° C.) | Viscosity (cSt) 40° C. | Viscosity (cSt) 100° C. | Viscosity Index | AV (mg/g) | FFA (%) | Gardner Color |
|---|---|---|---|---|---|---|---|---|
| Oleic acid 1 eq, levulinic 5 eq, HClO$_4$ 0.1 eq | −51 | −31 | 43.2 | 7.3 | 133 | 3.27 | 1.62 | 16+ |
| Oleic acid 1 eq, levulinic 5 eq, HClO$_4$ 0.1 eq | −51 | <−51 | 85.1 | 12.1 | 137 | 5.46 | 2.74 | 17+ |
| Oleic acid 1 eq, levulinic 5 eq, HClO$_4$ 0.1 eq | −51 | −19 | 29.0 | 5.5 | 129 | 9.78 | 4.92 | 5 |
| Castor oil 1 eq, levulinic 10 eq, Tin (II) ethylhexanoate 0.48%, temp inc to 150° C. | −33 | <−54 | 200.0 | 22.9 | 139 | 7.35 | 3.69 | 4− |
| 12-OH Stearic 2-EH esters 1 eq, levulinic 5 eq, Tin (II) ethylhexanoate 0.48% | −30 | −15 | 28.0 | 5.6 | 144 | 2.85 | 1.40 | 4+ |
| 12-OH Stearic 2-EH esters 1 eq, levulinic 5 eq, Tin (II) ethylhexanoate 0.48% | −42 | −39 | 29.7 | 5.8 | 142 | 2.50 | 1.25 | 6+ |
| 12-OH Stearic 2-EH esters 1 eq, levulinic 5 eq, Tin (II) ethylhexanoate 0.48% | −39 | −7 | 28.5 | 5.6 | 139 | 1.71 | 0.86 | 3 |
| 12-OH Stearic 2-EH esters 1 eq, levulinic 5 eq, Tin (II) ethylhexanoate 0.48% | −42 | −24 | 30.6 | 5.9 | 141 | 1.43 | 0.72 | 4+ |
| 12-OH Stearic 2-EH esters | >20 | >20 | 29.1 | 4.9 | 86 | 0.71 | 0.36 | 0 |
| Castor oil 1 eq, levulinic 10 eq, Tin (II) ethylhexanoate 0.48%, temp inc to 130° C. | −36 | <−50 | 177.1 | 20.8 | 138 | 7.68 | 3.83 | 3+ |
| Oleic acid 1 eq, levulinic 5 eq, HClO$_4$ 0.1 eq | −51 | −51 | 38.3 | 6.7 | 132 | 4.36 | 2.19 | 14− |
| Castor oil 1 eq, levulinic 10 eq, Tin (II) ethylhexanoate 0.48%, temp inc to 140° C. | −36 | <−50 | 174.5 | 20.8 | 140 | 9.60 | 4.82 | 3+ |
| Castor oil 1 eq, levulinic 10 eq, Tin (II) ethylhexanoate 0.48%, temp inc to 150° C. | −39 | — | 197.0 | 22.8 | 141 | 7.07 | 3.55 | 8+ |
| Oleic acid 1 eq, levulinic 5 eq, HClO$_4$ 0.1 eq | −45 | −14 | 40.5 | 6.9 | 129 | 4.41 | 2.22 | 16+ |
| Castor oil 1 eq, levulinic 10 eq, Tin (II) ethylhexanoate 0.48%, temp inc to 150° C., cond to 40° C. | −36 | <−36 | 177.3 | 20.9 | 139 | 12.70 | 6.39 | 4+ |
| 12-OH Stearic 2-EH esters 1 eq, levulinic 5 eq, Tin (II) ethylhexanoate 0.48% | −42 | −14 | 30.3 | 5.9 | 143 | 4.58 | 2.30 | 2 |
| 12-OH Stearic 2-EH esters 1 eq, levulinic 5 eq, Tin (II) ethylhexanoate 0.48% | −42 | −41 | 31.2 | 6.1 | 147 | 1.81 | 0.91 | 3+ |
| 19602-886 D distilled @ 140° C. | 6 | — | 23.3 | 4.8 | 130 | 2.25 | 1.13 | 11− |
| Dist of 935B-185C, distill @100° C. to remove levulinic, then @ 150° C. to remove 2-EH ester | 3 | 15 | 27.7 | 5.4 | 133 | 8.20 | 4.12 | 0 |
| Oleic acid 1 eq, levulinic 5 eq, HClO$_4$ 0.1 eq | −57 | <−57 | 38.0 | 6.9 | 142 | 2.38 | 1.19 | 14+ |
| Castor oil 1 eq, levulinic 10 eq, Tin (II) ethylhexanoate 0.48%, temp inc to 150° C., cond to 60° C. | −39 | <−39 | 172.5 | 20.9 | 143 | 9.34 | 4.70 | 2+ |
| Castor oil 1 eq, levulinic 10 eq, Tin (II) ethylhexanoate 0.48%, temp inc to 150° C., cond to 60° C. | −39 | — | 203.1 | 23.0 | 139 | 8.97 | 4.51 | 11− |

Example 7

In this example mixtures were tested using the same protocols discussed above.

TABLE 4

| Sample Name | Pour Pt (° C.) | Cloud Pt (° C.) | Viscosity (cSt) 40° C. | Viscosity (cSt) 100° C. | Viscosity Index | AV (mg/g) | FFA (%) | Gardner Color |
|---|---|---|---|---|---|---|---|---|
| 0:100; 12-OH stearic 2-EH esters:levulinic estolide | −42 | −26 | 30.9 | 6.0 | 144 | 1.57 | 0.79 | 5+ |
| 100:0; 12-OH stearic 2-EH esters:levulinic estolide | >20 | >20 | 29.6 | 4.9 | 81 | 0.40 | 0.20 | 0 |
| 50:50; 12-OH stearic 2-EH esters:levulinic estolide | 15 | >20 | 27.5 | 5.3 | 128 | 1.08 | 0.54 | 1+ |
| 25:75; 12-OH stearic 2-EH esters:levulinic estolide | 0 | 12 | 28.6 | 5.6 | 139 | 1.63 | 0.82 | 3 |
| 75:25; 12-OH stearic 2-EH esters:levulinic estolide | 18 | >20 | 27.8 | 5.0 | 105 | 0.71 | 0.35 | 0 |
| 10:90; 12-OH stearic 2-EH esters:levulinic estolide | −39 | 1 | 29.7 | 5.8 | 142 | 1.40 | 0.70 | 3+ |

Example 8

Table 5 shows comparative examples of physical properties for commercially available synthetic, petroleum-based, and bio-based alternatives. The same protocols were used as discussed above.

TABLE 5

| Commercial Products | Pour Point ° C. | Cloud Point ° C. |
|---|---|---|
| Synthetic #1 | −45 | −45 |
| Synthetic #2 | −41 | −42 |
| Synthetic #3 | −21 | −10 |

TABLE 5-continued

| Commercial Products | Pour Point ° C. | Cloud Point ° C. |
|---|---|---|
| Petroleum-Based #1 | −36 | −2 |
| Petroleum-Based #2 | −33 | 2 |
| Petroleum-Based #3 | −33 | −5 |
| Petroleum-Based #4 | −30 | −7 |
| Petroleum-Based #5 | −27 | 2 |
| Petroleum-Based #6 | −27 | −2 |
| Petroleum-Based #7 | −27 | 4 |
| Bio-Based #1 | −18 | 1 |
| Bio-Based #2 | −15 | −10 |

Discussion

Estolides prepared in accordance with the invention were evaluated against the properties of common basestocks. Viscometric properties determine the flow characteristics of the lubricants, their film thickness, and their ability to maintain a lubricating film under varying temperatures. In the lubricant industry these properties are determined by measuring kinematic viscosities using Cannon-Fenske viscometers and then assigned to viscosity grades. ISO 32 and ISO 46 grades are the most popular.

Advantages of the estolides of the invention are, for example, their high viscosity index (VI) and viscosity grade of ISO 46. This compares to properties of oleates and vegetable oils as well as other commercially available synthetic, petroleum-based, and bio-based fluids. These estolides would not need thickeners which are necessary for tridecyl adipate or PAO 2. Presence of polymer-based thickeners or viscosity modifiers may cause shear stability problems in formulated lubricants.

Low temperature properties are important for lubricant pumpability, filterability, and fluidity as well as cold cranking and startup. Pour point is the most common indicator of the low temperature behavior. Basestocks derived from vegetable oils usually cannot remain liquid in the cold storage test for more than 1 day, therefore, in addition to the pour point, the cold storage test is being developed by ASTM D02 to assess cold weather suitability of lubricants. The estolides of the invention have significantly better low temperature properties than trioleates, vegetable oils, or polyol esters of higher viscosities. As such, a major advantage of the levulinic-capped estolides of the invention are their unexpectedly low pour points.

Oxidative stability defines the durability of a lubricant as well as its ability to maintain functional properties during its use. Vegetable oil and oleate based lubricants usually suffer from poor oxidative stability. Oxidative stabilities of the estolides described by the invention are comparable to these of fully saturated materials such as PAOs, polyol esters and adipates. Vegetable oils and most fluids derived from them are clearly inferior to the estolides.

In general, the estolides of the invention are expected to have advantages over vegetable oils and oleates in their oxidative stability and low temperature properties, over low viscosity PAOs; and they are expected to have advantages over adipates, in volatility, viscometric properties and biodegradability.

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety, including any materials cited within such referenced materials. Furthermore, the invention encompasses any possible combination of some or all of the various embodiments and characteristics described herein and/or incorporated herein. In addition, the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 30%, preferably by as much as 20%, and more preferably by as much as 10% to a reference quantity, level, value, or amount.

The term "consisting essentially of" excludes additional method (or process) steps or composition components that substantially interfere with the intended activity of the method (or process) or composition. This term may be substituted for inclusive terms such as "comprising" or "including" to more narrowly define any of the disclosed embodiments or combinations/sub-combinations thereof. Furthermore, the exclusive term "consisting" is also understood to be substitutable for these inclusive terms.

"Optional" or "optionally" means that the subsequently described event or circumstance may or may not occur, and that the description includes instances in which said event or circumstance occurs and instances where it does not. For example, the phrase "optionally comprising a fortifying additive" means that the composition may or may not contain a fortifying additive and that this description includes compositions that contain and do not contain a fortifying additive.

By the term "effective amount" of a compound or property as provided herein is meant such amount as is capable of performing the function of the compound or property for which an effective amount is expressed. As is pointed out herein, the exact amount required will vary from process to process, depending on recognized variables such as the compounds employed and various internal and external conditions observed as would be interpreted by one of ordinary skill in the art. Thus, it is not possible to specify an exact "effective amount," though preferred ranges have been provided herein. An appropriate effective amount may be determined, however, by one of ordinary skill in the art using only routine experimentation.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims. Although any methods and materials similar or equivalent to those described herein can be used in the practice or testing of the present invention, the preferred methods and materials are herein described. Those skilled in the art may recognize other equivalents to the specific embodiments described herein which equivalents are intended to be encompassed by the claims attached hereto.

The claimed invention is:

1. A composition comprising at least one compound having the formula:

$$\text{CH}_3\text{C(CH}_2)_2\text{C} \overset{\displaystyle O}{\underset{\displaystyle \phantom{O}}{\|}} \overset{\displaystyle O}{\underset{\displaystyle \phantom{O}}{\|}} \left[ \begin{array}{c} O \\ | \\ \text{CH}_3(\text{CH}_2)_y\text{CHCH}_2(\text{CH})_z(\text{CH}_2)_x\text{C} \\ \phantom{xxxxxxxxxxxxxxxxxxxxxx} \backslash O \end{array} \right]_n$$

$$\text{CH}_3(\text{CH}_2)_y\text{CHCH}_2(\text{CH})_z(\text{CH}_2)_x\text{COOR}$$

wherein:
x is an integer from 1 to 11 and y is 14–(x+z), 16–(x+z), or 18–(x+z);
z is 0 or 2, and if z is 2 there is a C=C double bond between the respective carbons;
n is 0 or an integer from 1 to about 9;
R is selected from the group consisting of: CHR1R2, a residual fragment of lesquerella oil, a residual fragment of castor oil, a residual fragment of erucic oil, or combinations thereof;
R1 and R2 are independently selected from hydrogen and a saturated or unsaturated, branched or straight chain, and substituted or unsubstituted hydrocarbon chain of C-1 to C-36; and
wherein the predominant species of secondary ester linkage is at the 9 position if z=0, x=6, and y=8; 10 position if z=0, x=7, and y=7; 12 position if z=2, x=7, and y=5 or z=0, x=9, and y=5; 13 position if z=0, x=10, and y=8; 14 position if z=2, x=9, and y=5 or z=0, x=11 and y=5.

2. The composition of claim 1, wherein n is from 1 to about 5.

3. The composition of claim 1, wherein n is from 1 to about 3.

4. The composition of claim 1, wherein n is from 1 to about 2.

5. The composition of claim 1, wherein R is selected from the group consisting of: 2-methylhexyl, 2-ethylhexyl, and a backbone of a triglyceride.

6. The composition of claim 1, wherein R is a 2-ethylhexyl unit.

7. The composition of claim 1, wherein the predominant species of secondary ester linkage is at the 9 position.

8. The composition of claim 1, wherein the predominant species of secondary ester linkage is at the 10 position.

9. The composition of claim 1, wherein the predominant species of secondary ester linkage is at the 12 position.

10. The composition of claim 1, wherein the predominant species of secondary ester linkage is at the 13 position.

11. The composition of claim 1, wherein the predominant species of secondary ester linkage is at the 14 position.

12. The composition of claim 1, wherein the formula is:

$$\text{CH}_3\text{C(CH}_2)_2\text{C} \overset{\displaystyle O}{\underset{\displaystyle \phantom{O}}{\|}} \overset{\displaystyle O}{\underset{\displaystyle \phantom{O}}{\|}} \left[ \begin{array}{c} O \\ | \\ \text{CH}_3(\text{CH}_2)_5\text{CH(CH}_2)_{10}\text{C} \\ \phantom{xxxxxxxxxxxxxxxxxxxx} \backslash O \end{array} \right]_n$$

$$\text{CH}_3(\text{CH}_2)_5\text{CH(CH}_2)_{10}\text{COOR},$$

wherein n is 0 or an integer from 1 to about 9.

13. The composition of claim 1, wherein the formula is:

$$\text{CH}_3\text{C(CH}_2)_2\text{C} \overset{\displaystyle O}{\underset{\displaystyle \phantom{O}}{\|}} \overset{\displaystyle O}{\underset{\displaystyle \phantom{O}}{\|}} \left[ \begin{array}{c} O \\ | \\ \text{CH}_3(\text{CH}_2)_5\text{CHCH}_2\text{CH}=\text{CH(CH}_2)_7\text{C} \\ \phantom{xxxxxxxxxxxxxxxxxxxxxxxxxxx} \backslash O \end{array} \right]_n$$

$$\text{CH}_3(\text{CH}_2)_5\text{CHCH}_2\text{CH}=\text{CH(CH}_2)_7\text{COOR},$$

wherein n is 0 or an integer from 1 to about 9.

14. The composition of claim 1, wherein the formula is:

$$\text{CH}_3\text{C(CH}_2)_2\text{C} \overset{\displaystyle O}{\underset{\displaystyle \phantom{O}}{\|}} \overset{\displaystyle O}{\underset{\displaystyle \phantom{O}}{\|}} \left[ \begin{array}{c} O \\ | \\ \text{CH}_3(\text{CH}_2)_5\text{CH(CH}_2)_{12}\text{C} \\ \phantom{xxxxxxxxxxxxxxxxxxxx} \backslash O \end{array} \right]_n$$

$$\text{CH}_3(\text{CH}_2)_5\text{CH(CH}_2)_{12}\text{COOR},$$

wherein n is 0 or an integer from 1 to about 9.

15. The composition of claim 1, wherein the formula is:

$$\text{CH}_3\text{C(CH}_2)_2\text{C} \overset{\displaystyle O}{\underset{\displaystyle \phantom{O}}{\|}} \overset{\displaystyle O}{\underset{\displaystyle \phantom{O}}{\|}} \left[ \begin{array}{c} O \\ | \\ \text{CH}_3(\text{CH}_2)_8\text{CH(CH}_2)_{11}\text{C} \\ \phantom{xxxxxxxxxxxxxxxxxxxx} \backslash O \end{array} \right]_n$$

$$\text{CH}_3(\text{CH}_2)_8\text{CH(CH}_2)_{11}\text{COOR},$$

wherein n is 0 or an integer from 1 to about 9.

16. The composition of claim 1, wherein the formula is:

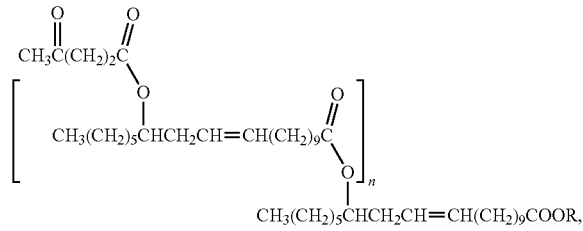

wherein n is 0 or an integer from 1 to about 9.

17. The composition of claim 1, wherein the formula is:

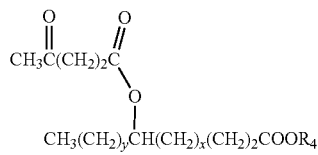

wherein $R_4$ is the residual fragment of erucic (x=9 and y=8 or x=10 and y=7) oil, saturated lesquerella (x=10 and y=5) oil, saturated castor (x=8 and y=5) oil, or combinations thereof.

18. The composition of claim 1 wherein the formula is:

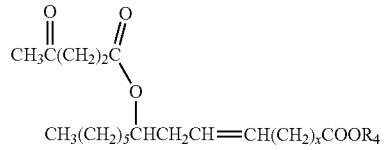

wherein $R_4$ is the residual fragment of saturated lesquerella (x=9) oil, saturated castor (x=7) oil, or combinations thereof.

19. The composition of claim 1, further comprising an effective amount of at least one other lubricating agent selected from the group consisting of: mineral or vegetable oils, other estolides, poly alpha olefins, polyol esters, oleates, diesters, other natural or synthetic fluids, and combinations thereof.

20. The composition of claim 1, further comprising at least one additive selected from the group consisting of: detergents, corrosion inhibitors, antioxidants, viscosity modifiers, friction modifiers, pour point depressants, dispersants, anti-foam agents, antimisting agents, wax crystal modifiers, dewaxing aids, colorants, and combinations thereof.

21. The composition of claim 1, wherein the pour point is from about −20° C. to about −55° C.

\* \* \* \* \*